US00PP30231P3

(12) United States Plant Patent
Ranney

(10) Patent No.: US PP30,231 P3
(45) Date of Patent: Feb. 26, 2019

(54) FLOWERING QUINCE PLANT NAMED 'NCCS4'

(50) Latin Name: *Chaenomeles speciosa*
Varietal Denomination: NCCS4

(71) Applicant: North Carolina State University, Raleigh, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 29 days.

(21) Appl. No.: 15/731,654

(22) Filed: Jul. 11, 2017

(65) Prior Publication Data

US 2019/0021195 P1 Jan. 17, 2019

(51) Int. Cl.
*A01H 5/02* (2018.01)

(52) U.S. Cl.
USPC ..... Plt./212
CPC ..... *A01H 5/02* (2013.01)

(58) Field of Classification Search
USPC ..... Plt./212
See application file for complete search history.

*Primary Examiner* — Anne Marie Grunberg
(74) *Attorney, Agent, or Firm* — Cassandra Bright

(57) ABSTRACT

A new and distinct cultivar of flowering quince shrub plant named 'NCCS4' is disclosed, characterized by double-flowers with peach-colored (reddish orange) petals, and thornless stems. Plants are medium-sized, spreading, multi-stemmed and fruitless. The new variety is a *Chaenomeles*, typically produced as an outdoor ornamental plant.

3 Drawing Sheets

Genus and species: *Chaenomeles speciosa.*
Variety denomination: 'NCCS4'.

BACKGROUND OF THE INVENTION

The present invention comprises a new and distinct cultivar of flowering quince, botanically known as *Chaenomeles speciosa*, and hereinafter referred to by the cultivar name 'NCCS4'. This new flowering quince was developed through a breeding program at North Carolina State University, Mills River, N.C. 'NCCS4' is an $F_1$ hybrid between the female parent, *Chaenomeles speciosa* 'Spitfire' (unpatented) and the male parent, *Chaenomeles speciosa* 'Dragons Blood' (unpatented). The first asexual propagation of 'NCCS4' was carried out in June 2003 by rooting stem cuttings at the North Carolina State University, Mountain Horticultural Crops Research Station, Mills River, N.C. and has been asexually reproduced repeatedly by vegetative cuttings in North Carolina over a fourteen-year period.

'NCCS4' roots readily from softwood cuttings treated with a basal dip of 5,000 ppm indole butyric acid (potassium salt) in water. 'NCCS4' has been found to retain its distinctive characteristics through successive asexual propagations. Plant Breeder's Rights for this cultivar have not been applied for in any foreign countries. 'NCCS4' has not been made publicly available more than one year prior to the filing date of this application. All access to plants has been directly derived from the inventor.

SUMMARY OF THE INVENTION

The following are the most outstanding and distinguishing characteristics of this new cultivar when grown under normal horticultural practices.

1. A medium-sized, spreading, multi-stemmed shrub.
2. Large, double-flowers with peach-colored (reddish orange) petals.
3. Thornless stems.
4. Fruitless.

COMPARISON WITH PARENTAL LINES

'NCCS4' is distinguished from the female parent, *Chaenomeles speciosa* 'Spitfire' (unpatented) in that 'Spitfire' has 5 petals, flowers with pistils, some thorns on stems, and produces fruit while 'NCCS4' has 11-13 petals, flowers without pistils, is thornless, and lacks fruit. 'NCCS4' is distinguished from the male parent *Chaenomeles speciosa* 'Dragons Blood' (unpatented) in that 'Dragons Blood' red flowers flowers while 'NCCS4' has peach-colored flowers. Table 1 shows the differences between 'NCCS4' and commercial varieties 'Jet Trail' (unpatented), 'Toyo-Nishiki' (unpatented), and 'Orange Storm' (U.S. Plant Pat. No. 20,950).

COMPARISON TO COMMERCIAL CULTIVARS

TABLE 1

| | Cultivar | | | |
|---|---|---|---|---|
| Trait | 'NCCS4' | 'Orange Storm' (U.S.Plant Pat. No. 20,950) | 'Jet Trail' (unpatented) | 'Toyo-Nishiki' (unpatented) |
| Flower color | Mostly reddish orange (RHS 34C to RHS N34D) | Orange, RHS 39A to RHS 44D | White, RHS N155 | Emerges White, RHS N155; Fading to Pink, RHS 49A to RHS 51C |

TABLE 1-continued

| Trait | Cultivar | | | |
|---|---|---|---|---|
| | 'NCCS4' | 'Orange Storm' (U.S.Plant Pat. No. 20,950) | 'Jet Trail' (unpatented) | 'Toyo-Nishiki' (unpatented) |
| Petal number per flower | 11 to 13 | 31 to 49 | 5 to 6 | 5 |
| Flower diameter | 4.0 cm to 6.0 cm | 4.5 cm to 6.5 cm | 5.0 cm to 6.0 cm | 3.0 cm to 5.6 cm |
| Pistil | Lacking | Lacking | Present | Generally Present |
| Fruit | Lacking | Lacking | Present | Present |
| Thorns | Lacking | Lacking | Lacking | Present |

DESCRIPTION OF THE PHOTOGRAPHS

This new quince plant is illustrated by the accompanying photographs which show the plant's form, foliage and inflorescences. The colors shown are as true as can be reasonably obtained by conventional photographic procedures.

Figure 1:
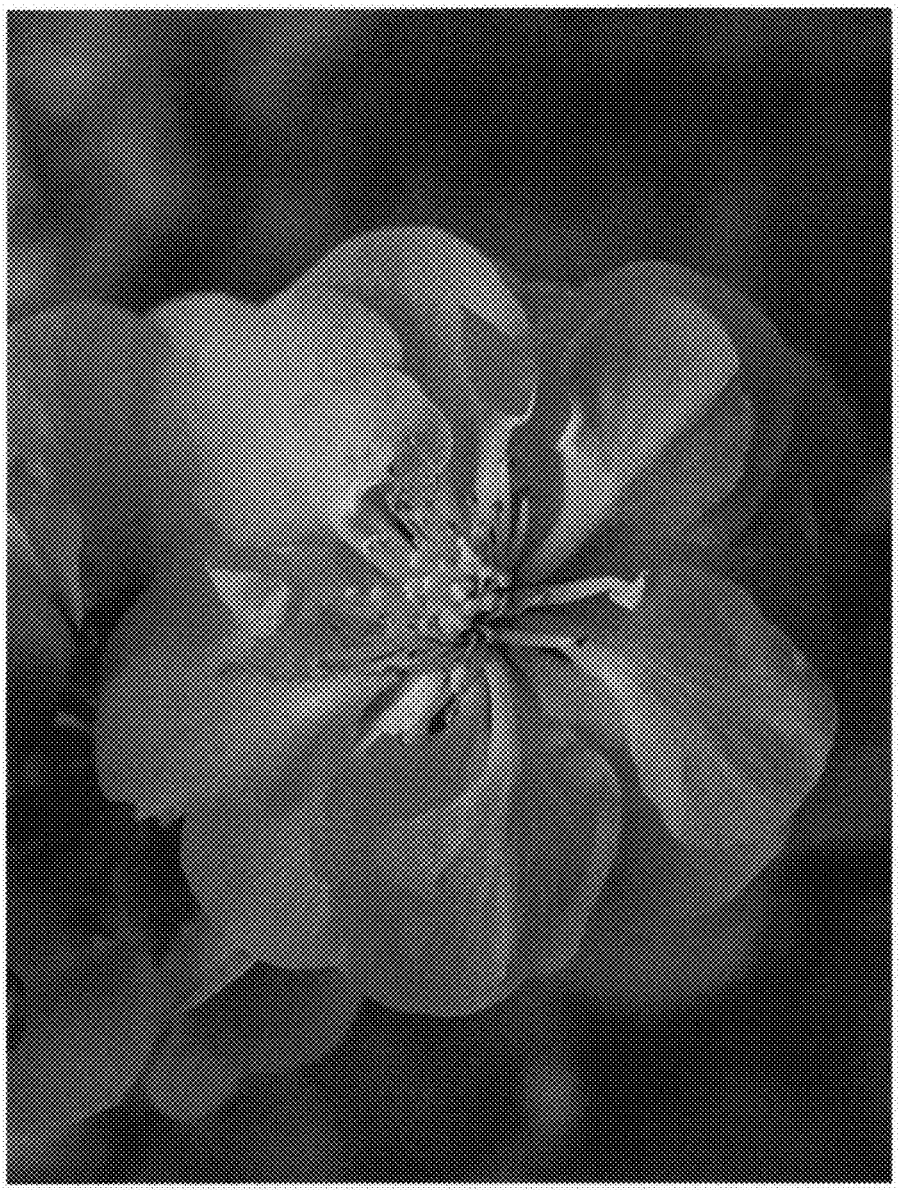
FIG. 1 shows a close-up of the, peach-colored, double flower, lacking a pistil, on a 2-year-old plant, taken on Mar. 30, 2007 in Mills River, N.C.
Figure 2:
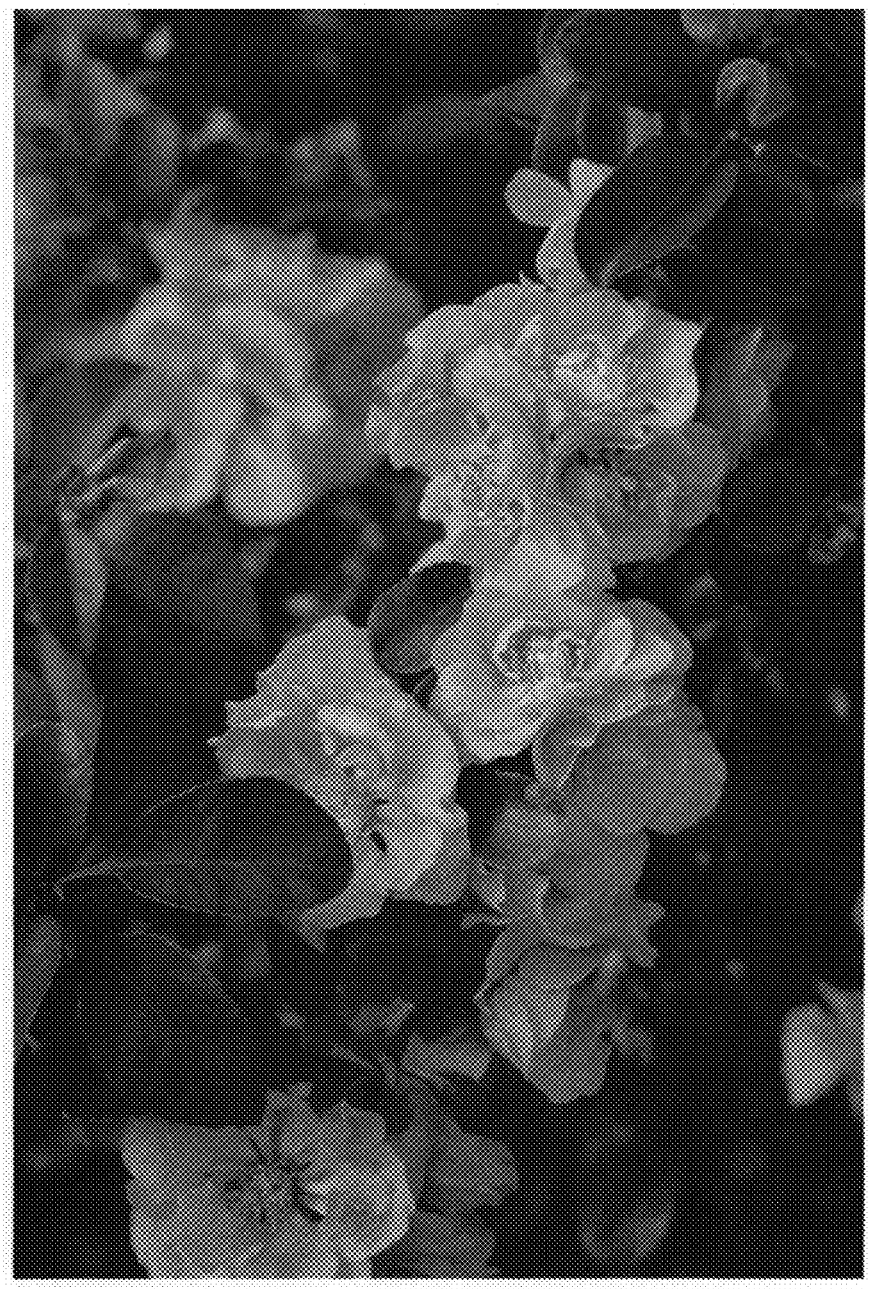
FIG. 2 shows a flowering shoot on a 2-year-old, container-grown plant, taken on May 6, 2016 in Grand Haven, Mich.
Figure 3:
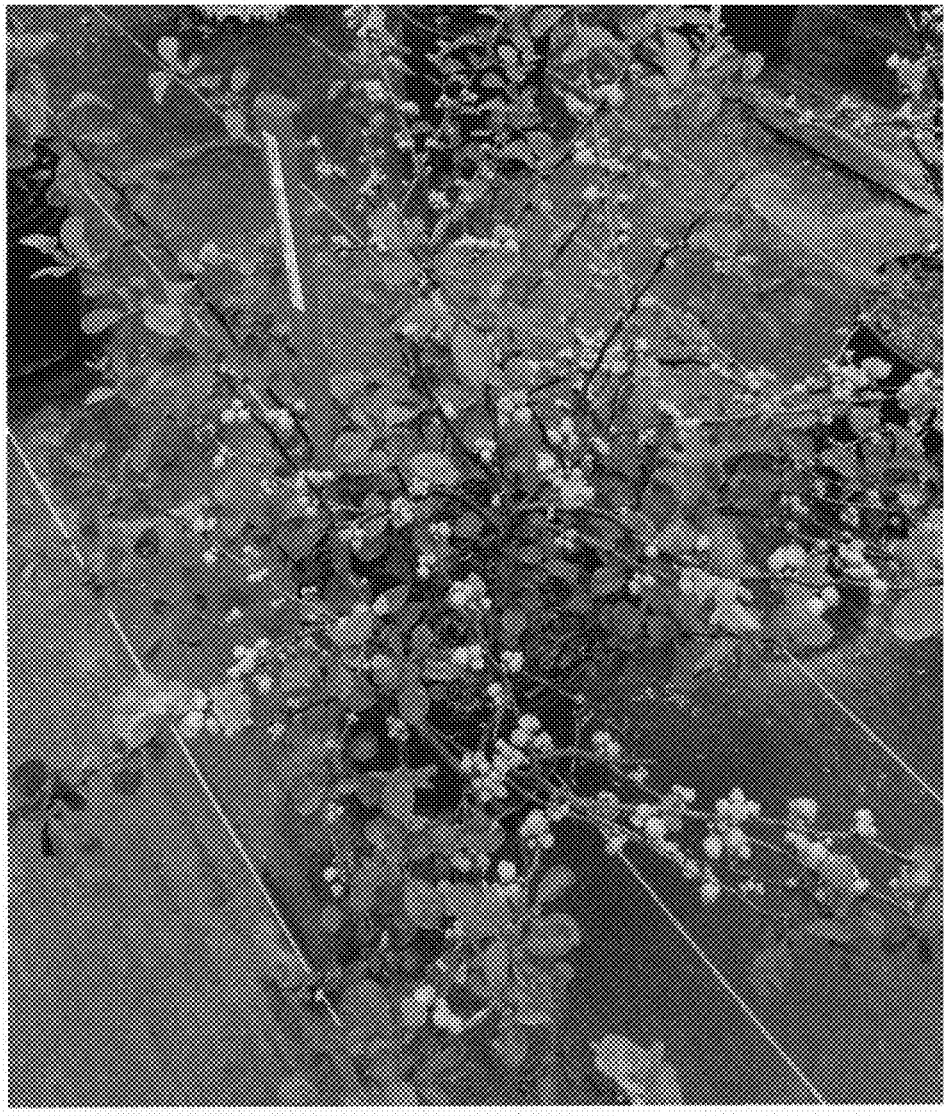

FIG. 3. shows a 2-year-old, container grown plant, with flower buds, taken on Apr. 30, 2016 in Grand Haven, Mich.

DETAILED BOTANICAL DESCRIPTION

The following detailed description sets forth the distinctive characteristics of 'NCCS4'. The detailed description was taken on 5-year-old plants growing under landscape conditions in Mills River, N.C. in April, 2017. Color references are for The R.H.S. Colour Chart, $6^{th}$ edition, of The Royal Horticultural Society of London (R.H.S.), 2015.

DETAILED BOTANICAL DESCRIPTION

Classification:

*Botanical name.*—*Chaenomeles speciosa.*

*Common name.*—Flowering Quince.

Parentage:

*Female parent.*—*Chaenomeles speciosa* 'Spitfire' (unpatented).

*Male parent.*—*Chaenomeles speciosa* 'Dragons Blood' (unpatented).

Plant description:

*Plant shape.*—Rounded/spreading.

*Height at maturity.*—Approximately 1.5 meters.

*Width at maturity.*—Approximately 2.0 meters.

Stem:

*Mature stem color.*—Variable, ranging from RHS N200B (Brownish grey) to RHS 199B (Dark greyish yellowish brown).

*Immature stem color.*—At tips, young stems are RHS 144A (Strong yellow green) but can blush in the sun to RHS 46B (Vivid red). Immature stems transition from 144A (Strong yellow green) into RHS 146C (Moderate yellow green) and RHS 199A (Moderate olive brown) as they age.

*Thorns.*—Thorns are absent.

Leaves:

*Type.*—Deciduous.

*Arrangement.*—Alternate.

*Division.*—Simple.

*Shape.*—Predominantly elliptic and obelliptic with occasional obovate or orbicular leaves.

*Apex.*—Rounded with some leaves exhibiting emarginate apices.

*Base.*—Attentuate.

*Margin.*—Serrulate.

*Mature leaf size.*—Length: Average is 3.14 cm (range 1.65-3.61 cm). Width: Average is 2.30 cm (range 1.44-3.87 cm).

*Immature leaf color and texture.*—Adaxial (upper) surface: New growth emerges as a mix of RHS N34A (Moderate red) and RHS 144A (Strong yellow green). Leaves transition to predominantly RHS 144A (Strong yellow green) as they continue to age, with red pigmentation persisting in some cases at the petiole/stem junction. Abaxial (lower) surface: New growth emerges as a combination of RHS N34A (Moderate red) and a Mix of RHS146B/C (Moderate yellow green) and RHS 147C (Moderate yellow green). As with the adaxial side, red pigmentation fades as leaves develop, but occasionally persists at the petiole/stem junction. Surface: Glabrous, both sides.

*Mature leaf color and texture.*—Adaxial (upper) surface: Variable, ranging from RHS NN137A (Greyish Olive Green) to RHS 137A (Moderate Olive Green). Abaxial (lower) surface: RHS N148A-148B (Moderate yellow green). Surface: Glabrous, both sides.

*Stipules* (*fully expanded; borne in pairs*).—Length: Average is 0.41 cm (range is 0.28-0.055 cm). Width: Average is 0.42 cm (range is 0.27-0.053 cm). Adaxial (upper) surface: RHS 137A (Moderate olive green). Abaxial (lower) surface: RHS 148B (Moderate yellow green). Surface: Glabrous, both sides.

*Leaf attachment.*—Petiolate.

*Petiole.*—Shape: Laterally compressed. Length: Average is 1.00 cm (range is 0.43-1.50 cm). Width: Average is 0.12 cm (range is 0.06-0.15 cm). Surface: Glabrous.

Flowers:

*Number of flowers per cluster.*—Average is 2.7 flowers per cluster (range is 1-4 flowers per cluster).

*Type.*—Double.

*Habit.*—Seasonal (spring).

*Flowering season.*—Early to late spring.

*Lastingness of flower on the plant.*—7-21 days.

*Fragrance.*—Absent.

*Self-cleaning or persistent.*—Self-cleaning.

*Flower.*—Diameter at anthesis: Average is 4.77 cm (range is 4.03-6.03 cm). Depth: Average is 2.53 cm (range is 2.00-3.00 cm). Petal number: Average is 12.2 petals (range is 11-13 petals).

*Petals.*—Length: Average is 2.41 cm (range is 1.94-2.91 cm). Width: Average is 2.09 cm (range is 1.85-2.56 cm). Color: Pre-anthesis: Adaxial (upper) surface: Ranges from RHS 34C (Strong reddish orange) to RHS N34D (Moderate reddish orange). Some petals exhibit deeper tones at tips into RHS N34C (Moderate red). Petals lighten to RHS 150C (Brilliant yellow green) at petal union point. Abaxial (lower) surface: same as adaxial surface. Surface:

Glabrous. Post-anthesis: Adaxial (upper) surface: RHS 34C (Strong reddish orange) transitions to RHS 31D (Moderate yellowish pink) near the petal interior, eventually lightening to RHS 155B (Greenish white) at petal base. Abaxial (lower) surface: same as adaxial surface. Surface: Glabrous. Petal shape: Flabellate. Apex: Rounded. Base: Cuneate. Margin: Entire. Fused or unfused: Unfused.

*Peduncle*.—Shape: Cylindrical. Length: Average is 0.84 cm (range is 0.57-1.27 cm). Width: Average is 0.13 cm (range is 0.12-0.14 cm). Color: A mix of RHS 144A/B (Strong yellow green). Surface: Glabrous.

Calyx/receptacle:

*Shape and arrangement*.—5-lobed and globular to globular conical.

*Diameter*.—Average is 1.58 cm (range is 0.57-2.04 cm).

*Depth*.—Average is 1.03 cm (range is 0.13-1.47 cm).

*Lobe length*.—Average is 0.47 cm (range is 0.25-0.62 cm)

*Lobe width*.—Average is 0.75 cm (range is 0.53-0.94 cm).

*Lobe number*.—5.

*Lobe apex*.—Truncate and often reflexed.

*Lobe base*.—Fused.

*Lobe margin*.—Cilliate.

*Lobe color*.—Adaxial (upper) surface: RHS 143D (Moderate yellow green); RHS 46B (Vivid red) around margins. Surface: Pubescent. Abaxial (lower) surface: same as adaxial surface. Surface: Glabrous.

Reproductive organs:

*Stamen*.—Quantity per flower: Average is 76.2 stamens per flower (range is 62-95 stamens per flower). Shape: Filament. Color at anthesis: RHS 150D (Yellow-green). Attachment: Dorsifixed. Length: Average is 0.92 cm (range is 0.49-1.22 cm). Width: Average is 0.05 cm (range is 0.04-0.07 cm).

*Anther*.—Shape: Ovoid. Color: RHS 5C (Greenish yellow) prior to dehiscing; dries to a range of RHS 165A (Moderate brown) to RHS 165B (Brownish orange). Length: Average is 0.10 cm (range is 0.09-0.12 cm). Width: Average is 0.07 cm (range is 0.06-0.09 cm). Pollen color: RHS 16B (Light orange yellow). Pollen amount: Moderate.

*Pistil*.—Absent.

*Ovary*.—Absent.

Fruit/seed: None observed.

Disease and insect resistance: No significant disease or insect pests have been observed.

What is claimed:

1. A new and distinct cultivar of quince plant as shown and described herein.

* * * * *